United States Patent
Shih et al.

(10) Patent No.: US 12,083,138 B2
(45) Date of Patent: Sep. 10, 2024

(54) METHODS TO REDUCE COMPLICATIONS OF INTRA-ARTICULAR STEROID

(71) Applicants: TAIWAN LIPOSOME CO., LTD., Taipei (TW); TLC BIOPHARMACEUTICALS, INC., South San Francisco, CA (US)

(72) Inventors: Sheue-Fang Shih, Taipei (TW); Po-Chun Chang, Taipei (TW); Ming-Ju Wu, Taipei (TW)

(73) Assignees: Taiwan Liposome Co., Ltd., Taipei (TW); TLC Biopharmaceuticals, Inc., South San Francisco, CA (US)

( * ) Notice: Subject to any disclaimer, the term of this patent is extended or adjusted under 35 U.S.C. 154(b) by 939 days.

(21) Appl. No.: 17/252,382

(22) PCT Filed: Jul. 8, 2019

(86) PCT No.: PCT/US2019/040794
§ 371 (c)(1),
(2) Date: Dec. 15, 2020

(87) PCT Pub. No.: WO2020/014118
PCT Pub. Date: Jan. 16, 2020

(65) Prior Publication Data
US 2021/0196733 A1 Jul. 1, 2021

Related U.S. Application Data

(60) Provisional application No. 62/839,231, filed on Apr. 26, 2019, provisional application No. 62/695,763, filed on Jul. 9, 2018.

(51) Int. Cl.
| | | |
|---|---|---|
| *A61K 31/685* | (2006.01) | |
| *A61K 9/00* | (2006.01) | |
| *A61K 31/573* | (2006.01) | |
| *A61K 31/683* | (2006.01) | |
| *A61P 19/02* | (2006.01) | |

(52) U.S. Cl.
CPC .......... *A61K 31/685* (2013.01); *A61K 9/0019* (2013.01); *A61K 31/573* (2013.01); *A61K 31/683* (2013.01); *A61P 19/02* (2018.01)

(58) Field of Classification Search
CPC .. A61K 31/685; A61K 9/0019; A61K 31/573; A61K 31/683; A61K 9/127; A61K 31/58; A61K 31/661; A61K 47/24; A61K 2300/00; A61P 19/02; A61P 29/00
See application file for complete search history.

(56) References Cited

U.S. PATENT DOCUMENTS

| 8,956,600 B2 | 2/2015 | Shih et al. |
| 2006/0147511 A1 | 7/2006 | Panzner et al. |
| 2013/0296267 A1 | 11/2013 | Kief |

FOREIGN PATENT DOCUMENTS

| WO | 2012/019009 A1 | 2/2012 |
| WO | 2013/119988 A1 | 8/2013 |
| WO | 2014/008469 A2 | 1/2014 |
| WO | 2016/118649 A1 | 7/2016 |

OTHER PUBLICATIONS

Kulkarni, A.R., "Buzzer-assisted plethysmometer for the measurement of rat paw volume." Ind J Pharm Edu Res 45.4 (2011): 324.*
Wallis, W. J., "Intraarticular volume and clearance in human synovial effusions." Arthritis & Rheumatism 28.4 (1985): 441-449.*
Gerwin, N., "Intraarticular drug delivery in osteoarthritis." Advanced drug delivery reviews 58.2 (2006): 226-242.*
Wernecke et al., "The Effect of Intra-articular Corticosteroids on Articular Cartilage : A Systematic Review", Orthopaedic Journal of Sports Medicine, vol. 3, No. 5, 2015.
International Search Report and Written Opinion of corresponding application PCT/US2019/040794.
Gross et al. "Liposomal dexamethasone-diclofenac combinations for local osteoarthritis treatment", J. Pharmaceutics, 2009, vol. 376, p. 84-91.
Hellmich et al. "Acute Treatment of Facet Syndrome by CT-Guided Injection of Dexamethasone-21-Palmitate Alone and in Combination with Mepivacaine", Clin. Drug Invest., 2004, vol. 24, p. 559-567.
Van den Hoven et al. "Liposomal Drug Formulations in the Treatment of Rheumatoid Arthritis", Molecular Pharmaceutics, 2011, vol. 8, p. 1002-1015.
Rauchhaus et al. "Separating therapeutic efficacy from glucocorticoid side-effects in rodent arthritis using novel, liposomal delivery of dexamethasone phosphate: long-term suppression of arthritis facilitates interval treatment", Arthritis Res. & Thera., 2009, vol. 11, R190.
Kikuchi et al. "Liposomes: Properties and Applications", Oil chemistry, 1985, vol. 34, No. 10, p. 784-798.
Nakazawa et al. "Corticosteroid treatment induces chondrocyte apoptosis in an experimental arthritis model and in chondrocyte cultures", Clinical and Experimental Rheumatology, 2002 , vol. 20, p. 773-781.
Alan J. Grodzinsky et al., Intra-articular dexamethasone to inhibit the development of post-traumatic osteoarthritis, Mar. 2, 2017, 406-411, 35(3), Journal of Orthopaedic Research.
Yihong Cs Lu et al., Effects of short-term glucocorticoid treatment on changes in cartilage matrix degradation and chondrocyte gene expression induced by mechanical injury, Sep. 2, 2011, 1-15, 13(5), Arthritis Res Ther.

(Continued)

*Primary Examiner* — John M Mauro
(74) *Attorney, Agent, or Firm* — Leason Ellis LLP (57) ABSTRACT

Provided are methods of treating joint pain, comprising administering to a subject in need of joint pain treatment an effective amount of a pharmaceutical composition comprising a lipid mixture comprising one or more lipids; and an effective amount of an intra-articular steroid or a pharmaceutically acceptable salt thereof, wherein the therapeutic efficacy of the intra-articular steroid is sustained but the side effects associated with the intra-articular steroid are reduced.

14 Claims, 4 Drawing Sheets

(56) References Cited

OTHER PUBLICATIONS

R. Black et al., Dexamethasone chondroprotective corticosteroid or catabolic killer?, Nov. 22, 2019, 246-263, vol. 38, European Cells and Materials.
Y. Li et al., Effects of insulin-like growth factor-1 and dexamethasone on cytokine-challenged cartilage: relevance to post-traumatic osteoarthritis, Nov. 11, 2014, 266-74, 23(2), Osteoarthritis and Cartilage.

\* cited by examiner

TLC599 Single Dose
Dog: 12 mg DSP
(eq. to 60 mg TA)

A1: 12 mg/knee at Day 8

A2: 12 mg/knee at Day 31

A3: 12 mg/knee at Day 91

TLC599 Repeated Doses
Rabbit: 1.2 mg DSP
(eq. to 6 mg TA)

B1: 1.2 mg/knee at Day 15

B2: 1.2 mg/knee at Day 31

B3: 2 ×1.2 mg DSP at Day 91

FIG. 2

FIG. 3

METHODS TO REDUCE COMPLICATIONS OF INTRA-ARTICULAR STEROID

TECHNOLOGY FIELD

The present invention is related to the method to treat joint pain and minimize the side effects of intra-articular steroid, by administering a pharmaceutical composition comprising a lipid mixture comprising one or more lipids; and an effective amount of a steroid or a pharmaceutically acceptable salt thereof.

BACKGROUND OF THE INVENTION

Intra-articular (IA) steroid therapy has been used for more than 50 years, with the rationale to reduce joint inflammation and pain by the local delivery of an anti-inflammatory agent. It has been shown to be effective at temporarily alleviating joint pain associated with osteoarthritis and other inflammatory disorders.

A few years after the use of IA steroid therapy, physicians have noted rapidly progressive degenerative arthritis in patients received IA steroid. Subsequent in vivo and in vitro study shows IA steroid causes progressive damages to the articular cartilage, including the breakdown and loss of proteoglycans, cyst in articular cartilage and chondrocyte apoptosis. Of the three steroids studied (hydrocortisone, triamcinolone and dexamethasone), dexamethasone was most effective to induce the chondrocyte apoptosis. (F. Nakazawa et al, "Corticosteroid treatment induces chondrocyte apoptosis in an experimental arthritis model and in chondrocyte cultures" Clinical and Experimental Rheumatology, 2002; 20: 773-781).

Recent human studies have further demonstrated the deleterious effect of IA steroid on articular cartilage, as steroids caused significantly greater cartilage volume loss and chondrotoxicity. For this reason, many physicians limit the use of steroids, particularly to corticosteroids, to 3 to 4 IA injections per year into any given joint (P. Wehling et al, "Effectiveness of intra-articular therapies in osteoarthritis: a literature review" Ther Adv Musculoskelet Dis. 2017 August; 9(8): 183-196). The effectiveness of a single IA steroid injection only lasts for 1 to 2 weeks. Moreover, little evidence of an effect of the IA steroid injection at over 4 weeks' post injection was observed. Accordingly, limiting the use of steroids to 3-4 IA injections per year causes a gap in therapeutic effect between IA injections and worsens the arthritis symptoms.

In view of the deficiencies outlined above, there is a need for IA steroid therapy for treating joint pain with satisfactory therapeutic efficacy, but with reduced side effect profile, especially a reduction of cartilage and/or chondrocyte damage. The present disclosure addresses this need and other needs.

BRIEF SUMMARY OF THE INVENTION

According to one embodiment of the present disclosure, pharmaceutical compositions for sustaining the therapeutic effect of intra-articular steroid (IA steroid) while reducing the side effects associated with the IA steroid are provided. The pharmaceutical composition comprises (a) a lipid mixture comprising one or more lipids; and (b) an effective amount of an IA steroid or a pharmaceutically acceptable salt thereof, wherein the side effect associated with the IA steroid is reduced compared to that of a pharmaceutical composition without the lipid mixture.

In another embodiment, the present disclosure is directed to the use of a pharmaceutical composition described herein for treating joint pain with reduced side effect associated with an IA steroid injection, by administering the pharmaceutical composition to a subject in need thereof, wherein the IA steroid associated side effects are reduced compared to the side effects induced by the IA steroid in a subject following articular administration of an immediate release or standard steroid formulation.

Also provided is a method to treat joint pain with reduced side effect associated with an articular steroid injection, comprising administering to a subject in need of joint pain treatment an effective amount of a pharmaceutical composition described herein, wherein the IA steroid induced side effects are reduced compared to the side effects induced by the IA steroid in a subject following articular administration of an immediate release or standard steroid formulation.

DETAILED DESCRIPTION OF THE INVENTION

Definition

As employed above and throughout the disclosure, the following terms, unless otherwise indicated, shall be understood to have the following meanings.

As used herein, the singular forms "a," "an," and "the" include the plural reference unless the context clearly indicates otherwise.

All numbers herein may be understood as modified by "about", which, when referring to a measurable value such as an amount, a temporal duration, and the like, is meant to encompass variations of ±10%, ±5%, ±1%, ±0.1%, ±0.01% from a specified value, as such variations are appropriate to obtain a desired amount of substance or period of time unless otherwise specified.

The term "articular injection" as used herein, encompasses local injection at or near the site of joint pain, intra-articular injection or periarticular injection.

An "effective amount," as used herein, refers to a dose of the pharmaceutical composition that is sufficient to reduce the symptoms and signs of disease causing the joint pain, such as pain, inflammation, stiffness and swelling of the joint, and to reduce the side effect associated with IA steroid injection. The reduction in the symptoms and signs of disease causing the joint pain can be about a 10%, 20%, 30%, 40%, 50%, 60%, 70%, 80%, 90%, 100%, or any amount of reduction in between as measured by an appropriate clinical scale.

The term "treating," "treated," or "treatment" as used herein includes preventative (e.g. prophylactic), slowing, arresting or reversing progressive structural tissue damage causing joint pain. Throughout this application, by treating is meant a method of reducing, alleviating, inhibiting or delaying joint pain or the complete amelioration of joint pain as detected by art-known techniques. These include, but are not limited to, clinical examination, imaging or analysis of serum or joint aspirate (for example, rheumatoid factors, erythrocyte sedimentation rate), to name a few. For example, a disclosed method is considered to be a treatment if there is about a 1%, 5%, 10%, 20%, 30%, 40%, 50%, 60%, 70%, 80%, 90% or 100% reduction of joint pain in a subject when compared to the subject prior to treatment or control subjects.

The term "subject" can refer to a vertebrate having joint pain or to a vertebrate deemed to be in need of treatment for joint pain. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The term "joint pain" refers to a joint disorder or condition that involves inflammation and/or pain of one or more joints. The term "joint pain," as used herein, encompasses a variety of types and subtypes of arthritis of various etiologies and causes, either known or unknown, including, but not limited to, rheumatoid arthritis, osteoarthritis, infectious arthritis, psoriatic arthritis, gouty arthritis, and lupus-related arthritis or painful local tissues affected by bursitis, tenosynovitis, epicondylitis, synovitis and/or other disorders.

"Pharmaceutically acceptable salts" of steroids of the present disclosure include salts of an acidic steroid formed with bases, namely base addition salts such as alkali and alkaline earth metal salts, such as sodium, lithium, potassium, calcium, magnesium, as well as 4 ammonium salts, such as ammonium, trimethyl-ammonium, diethylammonium, and tris-(hydroxymethyl)-methyl-ammonium salts. Similarly, acid addition salts, such as of mineral acids, organic carboxylic acids and organic sulfonic acids, e.g., hydrochloric acid, methanesulfonic acid, maleic acid, are also possible provided to a basic steroid.

Pharmaceutical Composition

In one aspect, the present disclosure provides a pharmaceutical composition comprising a lipid mixture comprising one or more lipids and an effective amount of a steroid or a pharmaceutically acceptable salt thereof. The pharmaceutical composition sustains the therapeutic efficacy of the IA steroid and reduces the side effects associated with the IA steroid. Side effects of IA steroid, include, but are not limited to chondrocyte damage, chondrocyte apoptosis, proteoglycan loss, cysts in articular cartilage, articular cartilage degradation or joint destruction. The assessment of side effects of IA steroid could be made for example but not limited to non-invasive examination, such as MRI. The reduction in side effects in a subject injected with IA steroid formulated with the pharmaceutical compositions described herein can range from 1%, 5%, 10%, 20%, 30%, 40%, 50%, 60%, 70%, 80%, 90% or 100% when compared with a subject injected with IA steroid formulated without the pharmaceutical compositions described herein, i.e., without a lipid mixture.

In one embodiment, the pharmaceutical composition further comprising at least one pharmaceutically acceptable excipient, diluent, vehicle, carrier, medium for the active ingredient, a preservative, cryoprotectant or a combination thereof.

In one embodiment, the pharmaceutical composition of the present disclosure is prepared by mixing one or more lipids, with or without cholesterol, and one or more buffers to form liposomes, lyophilizing the liposomes with one or more bulking agents to form a lipid mixture in a form of cake and reconstituting the lipid mixture cake with an aqueous solution containing the steroid to form a liposomal steroid composition, wherein the liposomal steroid composition comprises the lipid mixture and steroid in a non-associated form or in a form associated to the lipids. The term "non-associated form" refers to the steroid molecules separable via gel filtration from the phospholipid/cholesterol fraction of the pharmaceutical composition and provides immediate release component.

In another embodiment, the pharmaceutical composition of the present disclosure is prepared by mixing one or more lipids, with or without cholesterol, in a solvent then removing the solvent to form a lipid mixture in a form of powder or film and reconstituting the lipid mixture powder or film with an aqueous solution containing the steroid to obtain the pharmaceutical composition in a form of an aqueous suspension.

In some embodiments, the pharmaceutical composition of the present disclosure comprises about 10% to about 50% of lipid-associated steroid or about 50% to about 90% of non-associated steroid. In other embodiments, the weight ratio of the phospholipid and cholesterol in combination to the steroid is about 5-80 to 1. In yet another embodiment, the weight ratio of the phospholipid and cholesterol in combination to the steroid is about 5-40 to 1. For example, the weight ratio of the phospholipid and cholesterol in combination to the steroid can be about 5, 10, 15, 20, 25, 30, 35, 40, 45, 50, 55, 60, 65, 70, 75 or 80 to 1.

Lipid Mixture

The lipid mixture of the pharmaceutical composition provided herein refers to a lipid or a mixture of lipids. The lipid mixture is, but not limited to, in a form of film, cake, granules or powders.

In some embodiments, the lipid mixture comprises one or more lipids. Optionally, the one or more lipids include at least one neutral lipid and an anionic lipid at a mole percentage of 29.5% to 90%: 3% to 37.5%; alternatively at a mole ratio from 2:1 to 33:1.

In one embodiment, a phospholipid or a mixture of phospholipids, with or without cholesterol, are pre-formed into liposomes before further processing into the lipid mixture.

In another embodiment, a phospholipid or a mixture of phospholipids, with or without cholesterol, are not pre-formed into liposomes before further processing into the lipid mixture.

The liposomes are nano-sized and comprise a lipid unilayer or a lipid bilayer surrounding an internal agent-carrying component. Non-limiting examples of liposomes include small unilamellar vesicles (SUV), large unilamellar vesicles (LUV), multivesicular liposome (MVL) and multi-lamellar vesicles (MLV) or combinations thereof.

The lipid mixture can be prepared from a variety of lipids capable of either forming or being incorporated into a unilayer or bilayer structure. The lipids used in the present disclosure are a category of amphiphilic substances include, but not limited to, fatty acids, glycerolipids, phospholipids, sphingolipids, sterols, prenol lipids, sacchrolipids and polyketides. The examples of the one or more phospholipids include, but are not limited to, phosphatidylcholine (PC), phosphatidylglycerol (PG), phosphatidylethanolamine (PE), phosphatidylserine (PS), phosphatidic acid (PA), phosphatidylinositol (PI). In some embodiments, the one or more phospholipids include egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphatidylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), polyethyleneglycol distearoylphosphatidylethanolamine (PEG-DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI), and a mixture thereof.

In another embodiment, the lipid mixture includes a hydrophilic polymer with a long chain of highly hydrated flexible neutral polymer attached to a phospholipid molecule. Examples of the hydrophilic polymer include, but are not limited to, polyethylene glycol (PEG) with a molecular weight about 2,000 to about 5,000 daltons, methoxy PEG (mPEG), ganglioside $GM_1$, polysialic acid, polylactic acid (also termed polylactide), polyglycolic acid (also termed polyglycolide), polylacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers.

In one embodiment, the lipid mixture further comprises a sterol. Sterol used in the present disclosure is not particularly limited, but examples thereof include cholesterol, phytosterol (sitosterol, stigmasterol, fucosterol, spinasterol, brassicasterol, and the like), ergosterol, cholestanone, cholestenone, coprostenol, cholesteryl-2'-hydroxyethyl ether, and cholesteryl-4'-hydroxybutyl ether. The sterol component of the lipid mixture, when present, can be any of those sterols conventionally used in the field of liposome, lipid vesicle or lipid particle preparation. In another embodiment, the lipid mixture comprises of about 10% to about 33% of cholesterol, about 15 to less than about 30 mole % of cholesterol, about 18 to about 28 mole % of cholesterol or about 20 to about 25 mole % of cholesterol.

In some embodiments, the lipid mixture comprises a first phospholipid and a second phospholipid. In other embodiments, the first phospholipid is selected from DOPC, POPC, SPC, or EPC and the second phospholipid is PEG-DSPE or DOPG. In an exemplary embodiment, the lipid mixture comprises DOPC, DOPG and cholesterol at a mole percent of 29.5% to 90%: 3% to 37.5%: 10% to 33%.

In one embodiment, the lipid mixture is free of fatty acid or cationic lipid (i.e. a lipid carrying a net positive charge a physiological pH).

In some embodiments, the lipid mixture may further comprise a lipid-conjugate of an antibody or a peptide that acts as a targeting moiety to enable liposomes thereof to specifically bind to a target cell bearing a target molecule. Non-limiting examples of the target molecules include, but are not limited to, TNF-α and B cell surface antigen, such as CD20. Other antigens, such as CD19, HER-3, GD2, Gp75, CS1 protein, mesothelin, cMyc, CD22, CD4, CD44, CD45, CD28, CD3, CD123, CD138, CD52, CD56, CD74, CD30, Gp75, CD38, CD33, GD2, VEGF, or TGF may also be used.

The liposomes prepared in this disclosure can be generated by conventional techniques used to prepare vesicles. These techniques include the ether injection method (Deamer et al., Acad. Sci. (1978) 308: 250), the surfactant method (Brunner et al., Biochim. Biophys. Acta (1976) 455: 322), the freeze-thaw method (Pick et al., Arch. Biochim. Biophys. (1981) 212: 186), the reverse-phase evaporation method (Szoka et al., Biochim. Biophys. Acta. (1980) 601: 559 71), the ultrasonic treatment method (Huang et al., Biochemistry (1969) 8: 344), the ethanol injection method (Kremer et al., Biochemistry (1977) 16: 3932), the extrusion method (Hope et al., Biochim. Biophys. Acta (1985) 812:55 65), the French press method (Barenholz et al., FEBS Lett. (1979) 99: 210) and methods detailed in Szoka, F., Jr., et al., Ann. Rev. Biophys. Bioeng. 9:467 (1980). All of the above processes are basic technologies for the formation of vesicles and these processes are incorporated by reference herein. After sterilization, the pre-formed liposomes are placed aseptically into a container and then lyophilized to form a powder or a cake. In the embodiment where the lipid mixture comprising pre-formed liposomes, said liposomes are obtained by solvent injection method and followed by lyophilization to form the lipid mixture. The lipid mixture comprises one or more bulking agent. In one embodiment, the lipid mixture further comprises one or more buffering agents.

The bulking agents include, but are not limited to, polyols or sugar alcohols such as mannitol, glycerol, sorbitol, dextrose, sucrose, and/or trehalose; amino acids such as histidine, glycine. One preferred bulking agent is mannitol.

The buffering agents include, but are not limited to, sodium phosphate monobasic dihydrate and sodium phosphate dibasic anhydrous.

In the embodiment where the lipid mixture comprises lipids that are not pre-formed into liposomes, the lipid mixture can be prepared by dissolving in a suitable organic solvent, including, but not limited to, ethanol, methanol, t-butyl alcohol, ether and chloroform, and drying by heating, vacuum evaporation, nitrogen evaporation, lyophilization, or other conventional means of solvent removal.

Specific examples of lipid mixture preparation in support of the present disclosure will be described below.

Steroid for Articular Injection

The steroid in the pharmaceutical composition described herein includes a steroid suitable for articular injection or a pharmaceutically acceptable salt thereof. Examples of steroids include, but not limited to, corticosteroids, such as glucocorticoids and mineralocorticoids. In one embodiment, the steroid in the pharmaceutical composition described herein is a corticosteroid suitable for intra-articular (IA) injection.

The IA steroid useful in the present disclosure includes any naturally occurring steroid hormones, synthetic steroids and their derivatives. Examples of the IA steroid, derivatives or a pharmaceutically acceptable salt thereof include, but are not limited to, cortisone, hydrocortisone, hydrocortisone acetate, tixocortol pivalate, fluocinolone, prednisolone, methylprednisolone, prednisone, triamcinolone acetonide, triamcinolone, mometasone, amcinonide, budesonide, desonide, fluocinonide, fluocinolone acetonide, halcinonide, betamethasone, betamethasone sodium phosphate, dexamethasone, dexamethasone sodium phosphate (DSP), fluocortolone, hydrocortisone-17-butyrate, hydrocortisone-17-valerate, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, difluprednate, loteprednol, fluorometholone, medrysone rimexolone, beclomethasone, cloprednol, cortivazol, deoxycortone, difluorocortolone, fluclorolone, fluorocortisone, flumethasone, flunisolide, fluorocortolone, flurandrenolone, meprednisone, methylprednisolone, paramethasone or a mixture thereof. In an exemplary embodiment, the IA steroid is a water soluble steroid. In another exemplary embodiment, the IA steroid is selected from the Group B and Group C steroids according to Coopman Classification (S. Coopman et al., "Identification of cross-reaction patterns in allergic contact dermatitis from topical corticosteroids" Br J Dermatol. 1989 July; 121(1):27-34).

The pharmaceutically acceptable salts of the IA steroid include non-toxic salts formed from non-toxic inorganic or organic bases. For example, non-toxic salts can be formed with inorganic bases such as an alkali or alkaline earth metal hydroxide, e.g., potassium, sodium, lithium, calcium, or magnesium; and with organic bases such as an amine and the like.

The pharmaceutically acceptable salts of the IA steroid also include non-toxic salts formed from non-toxic inorganic or organic acids. Example of organic and inorganic acids are, for example, hydrochloric, sulfuric, phosphoric, acetic, succinic, citric, lactic, maleic, fumaric, palmitic, cholic, pamoic, mucic, D-glutamic, glutaric, glycolic, phthalic, tartaric, lauric, stearic, salicylic, sorbic, benzoic acids and the like.

The IA steroid can be administered at any effective amount by articular injection to reduce the symptoms or signs of arthritis. They may be administered at a dose ranging from about 0.1 mg to about 300 mg, from about 0.1 mg to about 100 mg, from about 0.1 mg to about 20 mg, from about 0.1 mg to about 18 mg, from about 1 mg to about 300 mg, from about 1 mg to about 100 mg, from about 1 mg to about 20 mg, from about 1 mg to about 18 mg, from about 4 mg to about 300 mg, from about 4 mg to about 100 mg, from about 4 mg to about 20 mg, from about 4 mg to about 18 mg. In some embodiments, the IA steroid of the pharmaceutical composition of the present disclosure is at a concentration ranging from about 1 mg to about 20 mg, from about 1 mg to about 18 mg, from about 4 mg to about 300 mg, from about 4 mg to about 100 mg, from about 4 mg to about 20 mg, or from about 4 mg to about 18 mg per milliliter (mL).

In some embodiments, the IA steroid of the pharmaceutical composition of the present disclosure is at a concentration of at least 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM or 35 mM; and optionally ranging from about 10 mM to about 40 mM, from about 15 mM to about 40 mM, 20 mM to about 40 mM, from about 15 mM to about 35 mM, from about 15 mM to about 30 mM, 15 mM to about 25 mM, or from about 20 mM to about 25 mM.

Useful dosages of IA steroid in human are determined by comparing their in vitro activity, and in vivo activity in animal models. Methods for the extrapolation of effective dosages in mice, and other animals, to humans are known in the art; for example, see U.S. Pat. No. 4,938,949, which is incorporated by reference herein.

The dosage of the IA steroid administered will depend on the severity of the condition being treated, the particular formulation, and other clinical factors such as weight and the general condition of the recipient and severity of the side effect.

The pharmaceutical composition may be administered in a single dose treatment or in multiple dose treatments, over a period of time appropriate to the condition being treated. The pharmaceutical composition may conveniently be administered at appropriate intervals, for example, once over a period of a week, two weeks, six weeks, a month, two months, at least 3 months, at least 6 months or until the symptoms and signs of the condition resolved. In a groups of embodiments, the multiple dose treatment by at least two articular injections are administered at a dosing interval selected from the group consisting of two weeks, three weeks, four weeks, five weeks, six weeks, seven weeks, eight weeks, night weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks and twenty-three weeks.

The IA steroid of the preset disclosure can be mixed either in $ddH_2O$ or a suitable buffer to form an aqueous solution containing the steroid for use in preparation of the liposomal steroid composition. In some embodiments, the IA steroid is water soluble and not covalently bound to a lipid including but not limited to sterol, phospholipid or fatty acid, such as palmitate. Suitable solubility of IA steroid in water is, for example, but not limited to at least 4 mg/mL, 10 mg/mL, 20 mg/mL, 30 mg/mL, 40 mg/mL or 50 mg/mL; optionally 4 mg/mL to 10 mg/mL; and 5 mg/mL to 60 mg/mL.

Methods of Treating Joint Pain or Inflammation and Reduce the Side Effect Associated with IA Steroid Typically, a subject's articular cartilage undergoes rapidly progressive degeneration or damage following IA administration of a steroid, such as corticosteroid. This is due to the side effects of IA steroid, including chondrocyte damage, chondrocyte apoptosis, proteoglycan loss, articular cartilage degradation or joint destruction.

One aspect of this disclosure is directed to a method of treating joint pain with minimal side effects of IA steroid in a subject, comprising the administration an effective amount of the pharmaceutical composition as described herein to a subject in need thereof, whereby the side effects induced by the IA steroid are reduced compared to the side effects in a subject following the administration of an immediate release or standard steroid formulation. In one embodiment, the subject has arthritis such as osteoarthritis, rheumatoid arthritis, acute gouty arthritis.

Also provided are methods for minimizing corticosteroid-induced arthropathy or side effects associated with IA steroid in a subject in need of treatment for joint pain, by administering the pharmaceutical composition disclosed herein.

In another aspect, the sustained, steady state release of the IA steroid from the pharmaceutical composition described herein does not induce articular cartilage damage or destruction.

The pharmaceutical composition provided herein can be used in combination with any of a variety of additional therapeutics, including but not limited to, analgesics (e.g., bupivacaine, ropivacaine, or lidocaine), hyaluronic acid preparations (e.g., Synvisc-One™), non-steroidal anti-inflammatory agent (e.g., ibuprofen), disease modifying agents (e.g., methotrexate) or biologics (e.g., etanercept, infliximab, adalimumab, certolizumab pegol, golimumab or rituximab). In some embodiments, the claimed pharmaceutical composition and additional therapeutic are formulated into a single therapeutic composition, and the claimed pharmaceutical composition and the additional therapeutic are administered simultaneously. Alternatively, the claimed pharmaceutical composition and the additional therapeutic are separate from each other, e.g., each is formulated into a separate therapeutic composition, and the claimed pharmaceutical composition and the additional agent are administered simultaneously, or at different times during a treatment regimen by the same route or different routes, as a single dose or multiple doses.

The following examples further illustrate the pharmaceutical compositions, methods or uses in accordance with the present disclosure. These examples are intended merely to be illustrative of the pharmaceutical compositions, methods or uses in accordance with the present disclosure and are not to be construed as being limiting.

Example 1: Preparation of the Lipid Mixture

A lipid solution was prepared by the solvent injection method. The lipids, including DOPC, DOPG and cholesterol, were combined at a mole percentage of 67.5:7.5:25 and dissolved in 99.9% ethanol at about 40° C. in a flask to form a lipid solution. A tabletop ultrasonic bath was used for lipid dissolution.

The dissolved lipid solution was added to 1.0 mM sodium phosphate solution at 100 mL/min by a peristaltic pump to form a pro-liposome suspension. The pro-liposome suspension was then passed 6 to 10 times through a polycarbonate membrane with a pore size of 0.2 μm. A liposome mixture was obtained and the liposomes had an average vesicle diameter of about 120-140 nm (measured by Malvern Zeta-Sizer Nano ZS-90, Malvern Instruments Ltd, Worcestershire, UK).

The liposome mixture was dialyzed and concentrated by a tangential flow filtration system with Millipore Pellicon 2 Mini Ultrafiltration Module Biomax-100C (0.1 m²) (Millipore Corporation, Billerica, MA, USA) and then sterilized using a 0.2 μm sterile filter.

The lipid concentration of the filtered liposome mixture was quantified by phosphorous assay and the filtered liposome mixture was formulated with mannitol at a concentration of 2% mannitol and then sterilized again using a 0.2 μm sterile filter. The sterilized liposome mixture was then subject to lyophilization to obtain a lipid mixture in a form of cake.

Example 2: Preparation of the Pharmaceutical Composition

A pharmaceutical composition in accordance with the present disclosure was prepared by mixing the lipid mixture described in Example 1 with a DSP solution, which comprises 13.2 mg/ml dexamethasone sodium phosphate (DSP) ($C_{22}H_{28}FNa_2O_8P$; molecular weight: 516.41 g/L) and 4 mg/ml sodium citrate, whereby a liposomal DSP composition with the final concentration of DSP being 12.0 mg/ml (23.2 mM) was obtained.

Example 3. In Vivo Evaluation of the Pharmaceutical Composition in Reducing the Side Effects of Different Doses of Articular Steroid An in vivo study was performed using beagle dogs to evaluate the effectiveness of the pharmaceutical composition in reducing the side effects of different doses of IA steroid. A vehicle control was prepared by mixing the lipid mixture described in Example 1 with a solution comprising 0.9% sodium chloride.

The beagle dogs were divided into five groups and received the following IA injections in each knee:

Group A (n=8): a single IA injection of saline (0.9% sodium chloride in 1.5 mL per knee);

Group B (n=8): a single IA injection of the vehicle control (a suspension of the lipid mixture without DSP in 1.5 mL per knee)

Group C (n=8): a single IA injection of the liposomal DSP composition of Example 2 (4 mg DSP in 0.34 mL pharmaceutical composition per knee).

Group D (n=8): a single IA injection of the liposomal DSP composition of Example 2 (12 mg DSP in 1.0 mL pharmaceutical composition per knee)

Group E (n=8): a single IA injection of the liposomal DSP composition of Example 2 (18 mg DSP in 1.5 mL pharmaceutical composition per knee)

The beagle dogs were sacrificed 3 months after the IA injection of the testing composition in each knee. Toluidine blue staining was used to assess the loss of proteoglycan in the knee cartilage. The severity of proteoglycan loss is scored based on the following criteria:

Score 0: no proteoglycan loss
Score 1: minimal proteoglycan loss
Score 2: slight proteoglycan loss
Score 3: moderate proteoglycan loss
Score 4: marked proteoglycan loss
Score 5: severe proteoglycan loss Table 1 shows the degree of proteoglycan loss is similar among the groups of the liposomal DSP composition at various dose amounts (Groups C, D, and E), regardless of the dose of the DSP. After the dogs had received a single IA injection of the liposomal DSP composition (dose ranged from 4 mg to 18 mg) in each knee, 75% to 100% of the knee cartilages showed no to minimal proteoglycan loss, which is similar to that of the saline control group, with 100% of the knee cartilages showed no to minimal proteoglycan loss (Group A).

TABLE 1

Proteoglycan loss score of Groups A-E

| Group | Score | % of knees |
| --- | --- | --- |
| A | 0 | 12/16 = 75% |
|   | 1 | 4/16 = 25% |
|   | 2 | 0 |
|   | 3 | 0 |
|   | 4 | 0 |
|   | 5 | 0 |

TABLE 1-continued

Proteoglycan loss score of Groups A-E

| Group | Score | % of knees |
|---|---|---|
| B | 0 | 14/16 = 88% |
|   | 1 | 1/16 = 6% |
|   | 2 | 1/16 = 6% |
|   | 3 | 0 |
|   | 4 | 0 |
|   | 5 | 0 |
| C | 0 | 11/16 = 69% |
|   | 1 | 4/16 = 25% |
|   | 2 | 1/16 = 6% |
|   | 3 | 0 |
|   | 4 | 0 |
|   | 5 | 0 |
| D | 0 | 11/16 = 69% |
|   | 1 | 5/16 = 31% |
|   | 2 | 0 |
|   | 3 | 0 |
|   | 4 | 0 |
|   | 5 | 0 |
| E | 0 | 6/16 = 37.5% |
|   | 1 | 6/16 = 37.5% |
|   | 2 | 4/16 = 25% |
|   | 3 | 0 |
|   | 4 | 0 |
|   | 5 | 0 |

Example 4. Toxicity/Toxicokinetic Profile and Pharmacokinetic Profile of the Pharmaceutical Composition The object of the current example was to evaluate the cartilage damage of the liposomal DSP composition of Example 2 in comparison to current steroid treatment such as triamcinolone acetonide (TA) and triamcinolone acetonide extended-release injectable suspension (ER-TA) as well as toxicokinetic (TK)/pharmacokinetic (PK) profiles of the liposomal DSP composition of Example 2 following IA injection in five preclinical studies of healthy dogs and rabbits.

In four toxicity studies, cartilage histology was examined following IA injection of the liposomal DSP composition (denoted as TLC599) or other test articles. Proteoglycan loss was evaluated by cationic dyes, toluidine blue, that staining proteoglycans. The reduction in proteoglycan staining intensity would suggest cartilage damage and underlying chondrotoxicity. In two TK/PK studies, dexamethasone phosphate (DP) concentration was quantified and the TK/PK profile was evaluated (Table 2). DSP is the sodium salt form of DP.

TABLE 2

Non-clinical studies list

| Study | Animal species | Study designs |
|---|---|---|
| #8351851 | Dogs | The potential systemic and local knee toxicology and the TK profile of DP were assessed following single administration (once on day 1) or multiple administrations (once on Days 1, 93, 183, and 274). Knees of dogs were dosed with IA injections of saline, vehicle control, TLC599 at dose levels of 4, 12, 18 mg/knee, respectively. |
| #8388198 | Dogs | Joint tissues were collected at Day3, 92 and 276 to evaluate cartilage damage (acute phase, Day 3 and 276) as well as chance of recovery (Day 92). Synovial fluid was collected at 2.5, 48, 96, 168, and 360 hours post last dose. TLC599 was administered IA into knees of dogs (single dose; 18 mg/knee, 36 mg/animal). Synovial fluid was collected at 15, 30, 45, 90, and 120 days post-dose. |
| #8351850 | Dogs | TLC599 was administered IA into knees of dogs (single dose; 12 mg/knee). |
| #8288836 | Rabbits | TLC599 was administered IA into knees of rabbits (single dose or repeat dose after 1 month; 1.2 mg/knee). |
| #75903-18-214 | Dogs | TLC599 was compared with two marketed products- Triamcinolone Acetonide (TA) Injectable Suspension and Triamcinolone Acetonide Extended-Release (ER-TA) Injectable Suspension. Knees of dogs were dosed with a single IA injections of saline, a higher (18.75 mg/knee) and lower (2.1 mg/knee) dose of TA, a higher (18.75 mg/knee) and lower (2.1 mg/knee) dose of ER-TA, or 12 mg/knee of TLC599 (potency is equivalent to 60 mg TA by calculation). |

Figure 1A:
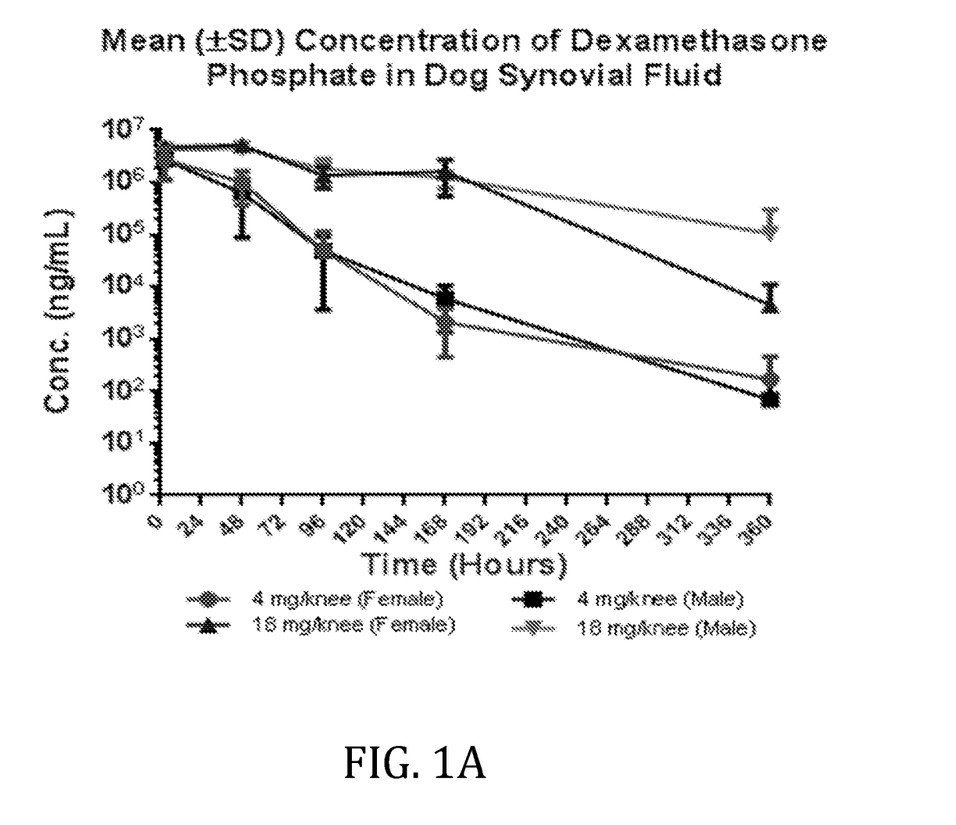
FIG. 1A to 1B are toxicokinetic profiles of the liposomal DSP composition following single-dose IA injection in dogs (study #8351851 and #8388198)

FIG. 1A shows mean concentration of dexamethasone phosphate in dog synovial fluid, wherein the synovial fluid were sampled at 2.5, 48, 96, 168, and 360 hours after single-dose IA injection of liposomal DSP composition at dose level of 4 and 18 mg/knee in both knees of female and male dogs.

Figure 1B:
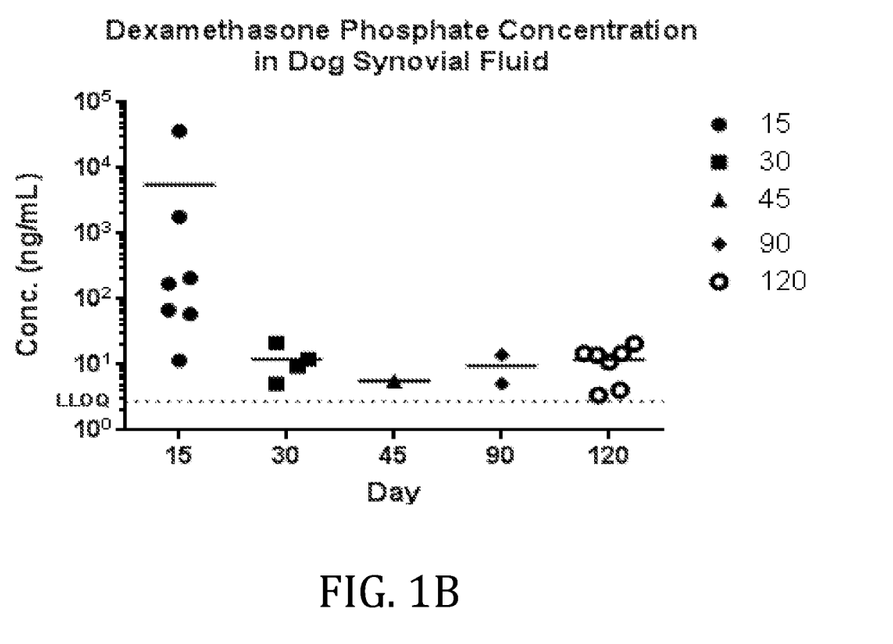

FIG. 1B shows dexamethasone phosphate concentration in dog synovial fluid, wherein the synovial fluid were sampled at 15, 30, 45, 90, and 120 days after single-dose IA injection of TLC599 at dose level 18 mg/knee (total 36 mg/animal) in both knees.

Following IA injection of the liposomal DSP composition, the concentration of DP in synovial fluid maintained in high level between 2.5 to 48.0 hours, and lasted through 360 hours (FIG. 1A). DP maintained at similar levels from 30 days to 120 days post-dose (FIG. 1B), demonstrating the prolonged local exposure in the joint.

Figure 2:
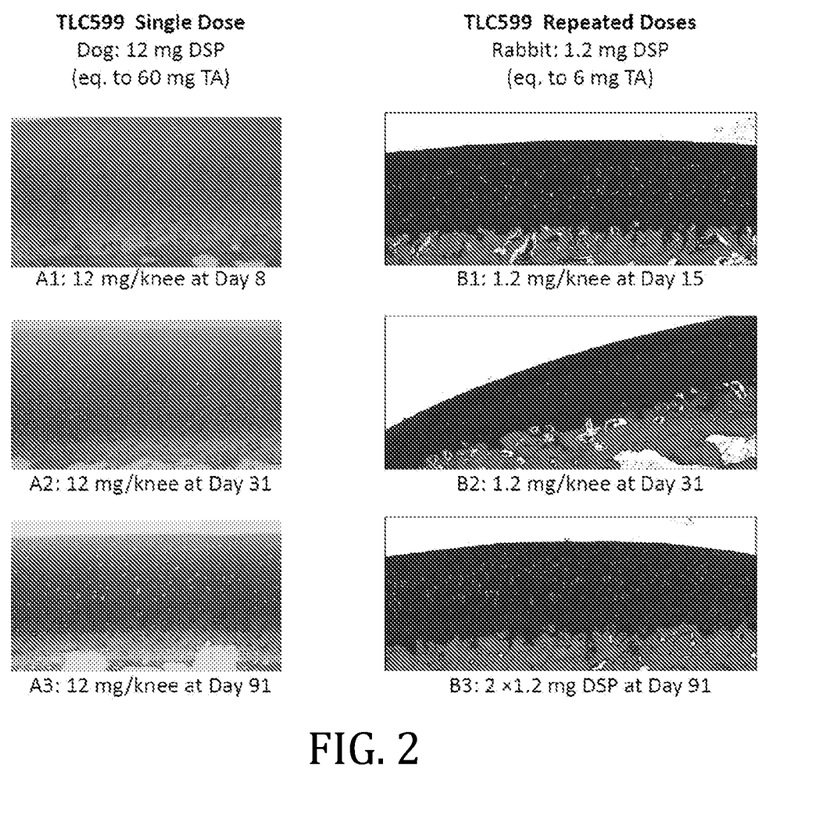
FIG. 2 illustrates toluidine blue staining of the cartilage in dogs (Study #8351850) and rabbits (Study #8288836) post treatment with single or multiple doses of liposomal DSP composition.

Toluidine blue staining of the cartilage in dogs (Study #8351850) and rabbits (Study #8288836) post treatment with single or multiple doses of liposomal DSP composition are shown in FIG. 2. In Study #8351850, dogs were dosed with 12 mg/knee of the liposomal DSP composition in knee joints and sacrificed at Day 8 (panel A1), Day 31 (panel A2), and Day 91 (panel A3) post treatment. In Study #8288836, rabbits were dosed with 1.2 mg/knee of the liposomal DSP composition in knee joints singly and sacrificed at Day 15 (panel B1) and day 31 (panel B2) post treatment; and rabbits were dosed twice (second dose in one month after) with 1.2 mg/knee of the liposomal DSP composition in knee joints and sacrificed at Day 91 (panel B3) post treatment.

As shown in FIG. 2, no intensity change of toluidine blue staining and morphology change of hematoxylin and eosin (H&E) staining were observed in both dogs and rabbits studies, indicating neither proteoglycan loss or cartilage damage even after repeat dosing.

Figure 3:
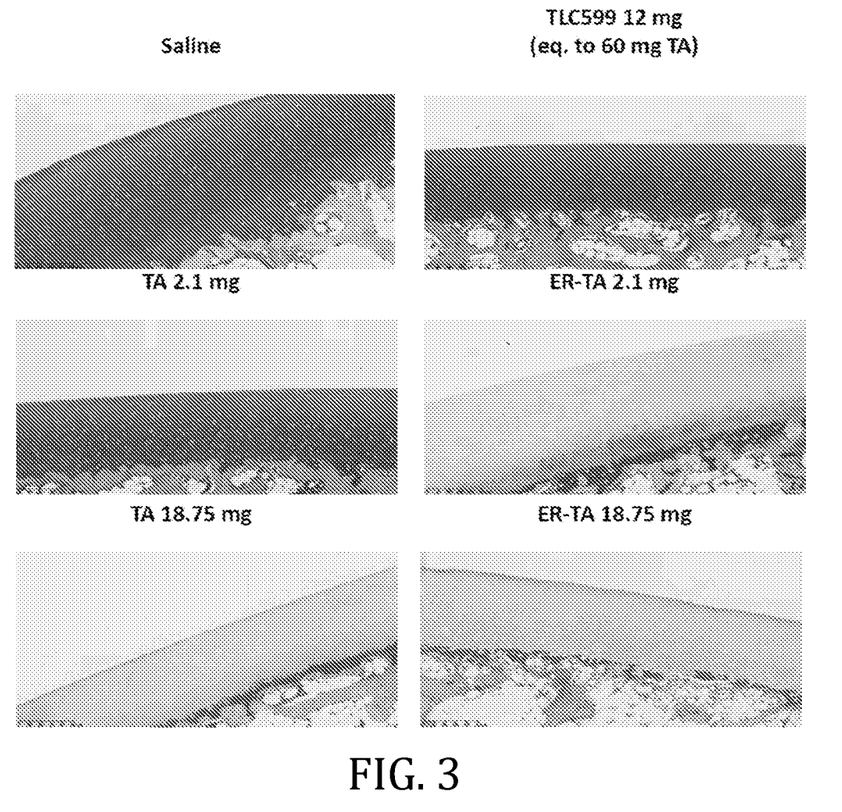
FIG. 3 illustrates toluidine blue staining of the cartilage in dogs (Study #79503-18-214) post treatment with the liposomal DSP composition (TLC599), triamcinolone acetonide (TA), triamcinolone acetonide extended-release injectable suspension (ER-TA) or saline as control.

Toluidine blue staining of the cartilage in dogs (Study #75903-18-214) post treatment with single dose of high dose TA and ER-TA are shown in FIG. 3. High dose TA and ER-TA showed a significantly proteoglycan loss compared to saline and low dose ER TA showed a significantly proteoglycan loss compared to its equipotent dose of TA, as well as saline (FIG. 3). In contrast, the liposomal DSP composition (denoted as TLC599) demonstrated comparable level of proteoglycan to that of saline at 30 days post treatment (FIG. 2).

Accordingly, ER-TA was observed to result in more proteoglycan loss and underlying chondrotoxicity than TA alone, particularly to at lower dose level (2.1 mg/knee). This data indicated that the liposomal DSP composition is significantly less toxic than the two conventional products.

In Study #75903-18-214, dogs were dosed with saline, 2.1 mg/knee and 18.75 mg/knee of triamcinolone acetonide (TA) (denoted as "TA 2.1 mg" and "TA 18.75 mg" respectively), 2.1 mg/knee and 18.75 mg/knee of triamcinolone acetonide extended-release injectable suspension (denoted as "ER-TA 2.1 mg" and "ER-TA 18.75 mg" respectively), or 12 mg/knee of the liposomal DSP composition in knee joints [denoted as "TLC599 12 mg (eq. to 60 mg TA)"]

In Study #8351851, no significant difference of Toxicity and TK profiles between the first dose of the liposomal DSP composition and the last dose of the liposomal composition was observed in dogs after 4 repeated doses of the liposomal DSP composition, suggesting that similar cartilage safety profile between the multiple-dose and the single-dose administration. The liposomal DSP composition can be administered repeatedly without significant side effect and is a safe and effective treatment in the long-term management of OA.

The liposomal DSP composition as the pharmaceutical composition in accordance with the present disclosure, a novel extended-release formulation of DSP, showed high level exposure of DSP in joint after single IA injection and maintained at similar levels up to four months (FIG. 1B).

No marked cartilage toxicity in preclinical dog and rabbit studies was observed after single-dose and multiple-dose IA injection of the liposomal DSP composition. In contrast, a moderate proteoglycan loss in cartilage was observed for both single dose TA and single dose ER-TA (FIG. 3).

What is claimed is:

1. A method of treating joint pain and reducing side effects induced by an intra-articular (IA) steroid, comprising administering to a subject in need of treatment for joint pain an effective amount of a pharmaceutical composition comprising
    (a) a lipid mixture comprising a first phospholipid, a second phospholipid and a cholesterol at a mole percent ratio of 29.5% to 90%:3% to 37.5%:10% to 33%; and
    (b) an effective amount of the IA steroid or a pharmaceutically acceptable salt thereof, wherein the IA steroid or pharmaceutically acceptable salt thereof is at a concentration ranging from about 15 mM to about 40 mM; and wherein the pharmaceutical composition is administered via a dosing regimen having at least two intra-articular injections with a dosing interval of at least four weeks.

2. The method of claim 1, wherein the side effects are selected from the group consisting of chondrocyte damage, chondrocyte apoptosis, proteoglycan loss, cysts in articular cartilage, articular cartilage degradation, joint destruction or combinations thereof.

3. The method of claim 1, wherein the first phospholipid is 1,2-dioleoyl-sn-glycero-3-phosphatidylcholine (DOPC), 1-palmitoyl-2-oleoyl-sn-glycero-3-phosphatidylcholine (POPC), soy phosphatidylcholine (SPC), or egg phosphatidylcholine (EPC), and wherein the second phospholipid is polyethyleneglycol distearoylphosphatidylethanolamine (PEG-DSPE) or dioleoylphosphatidylglycerol (DOPG).

4. The method of claim 1, wherein the first phospholipid is DOPC, and wherein the second phospholipid is DOPG.

5. The method of claim 1, wherein the IA steroid is a water soluble steroid.

6. The method of claim 1, wherein the IA steroid is at a concentration ranging from about 15 mM to about 30 mM.

7. The method of claim 1, wherein the IA steroid is a corticosteroid.

8. The method of claim 1, wherein the IA steroid is dexamethasone sodium phosphate, dexamethasone, betamethasone, betamethasone sodium phosphate, betamethasone acetate, betamethasone dipropioinate, betamethasone valerate, mometasone furonate, triamcinolone acetonide, triamcinolone hexacetonide, triamcinolone diacetate, methylprednisolone sodium succinate, methylprednisolone acetate, prednisolone tebutate, hydrocortisone acetate, alclometasone dipropionate, halcinonide, fluocortolone, fluocinolone acetonide or a combination thereof.

9. The method of claim 1, wherein the joint pain is caused by rheumatoid arthritis, osteoarthritis, infectious arthritis, psoriatic arthritis, gouty arthritis, lupus-related arthritis, bursitis, tenosynovitis, epicondylitis, or synovitis.

10. The method of claim 1, wherein the IA steroid is administered at a dose of about 8 mg to about 18 mg.

11. The method of claim 1, wherein the at least two intra-articular injections are administered at a dosing interval selected from the group consisting of four weeks, five weeks, six weeks, seven weeks, eight weeks, nine weeks, ten weeks, eleven weeks, twelve weeks, thirteen weeks, fourteen weeks, fifteen weeks, sixteen weeks, seventeen weeks, eighteen weeks, nineteen weeks, twenty weeks, twenty-one weeks, twenty-two weeks and twenty-three weeks.

12. The method of claim 1, wherein at least two intra-articular injections are administered at a dosing interval of about 10 to 14 weeks, and wherein the IA steroid per each intra-articular injection is at a dose of 8 mg to 18 mg dexamethasone sodium phosphate.

13. The method of claim 1, wherein the IA steroid is at a concentration ranging from about 20 mM to about 25 mM.

14. A pharmaceutical composition for treating joint pain or inflammation, wherein the pharmaceutical composition comprises:
    (a) a lipid mixture comprising DOPC, DOPG and cholesterol at a mole percent ratio of 29.5% to 90%:3% to 37.5%:10% to 33%; and
    (b) an IA steroid or a pharmaceutically acceptable salt thereof,
    wherein the IA steroid is dexamethasone sodium phosphate at a dose ranging from 10 mg to 14 mg with a concentration ranging from about 15 mM to about 40 mM; and
    wherein the pharmaceutical composition is administered via a dosing regimen having at least two intra-articular injections with a dosing interval of at least four weeks.

* * * * *